United States Patent [19]

Swallow

[11] 4,441,900
[45] Apr. 10, 1984

[54] METHOD OF TREATING CARBON-DIOXIDE-CONTAINING NATURAL GAS

[75] Inventor: Brian R. Swallow, Media, Pa.

[73] Assignee: Union Carbide Corporation, Danbury, Conn.

[21] Appl. No.: 381,846

[22] Filed: May 25, 1982

[51] Int. Cl.³ .............................................. F25J 3/04
[52] U.S. Cl. .......................................... 62/29; 62/31; 62/34; 62/39
[58] Field of Search ...................... 62/9, 11, 12, 19, 23, 62/24, 27–29, 31–34, 38, 39, 42, 43; 55/17, 68, 69

[56] References Cited

U.S. PATENT DOCUMENTS

3,130,026  4/1964  Becker ..................................... 62/24
4,252,548  2/1981  Markbreiter ............................ 62/23

Primary Examiner—Frank Sever
Attorney, Agent, or Firm—Saul R. Bresch

[57] ABSTRACT

A cryogenic separation process for rejecting carbon dioxide from a carbon-dioxide-containing natural gas mixture. The invention is specifically designed for treating a natural gas mixture recovered from a petroleum well employing the enhanced recovery technique of carbon dioxide flooding. The carbon-dioxide-containing natural gas mixture is treated using a particular arrangement of fractional condensation, partial vaporization and rectification unit operations to produce an enriched-methane gas stream and carbon dioxide product streams at various pressures. The invention is well suited for the bulk separation of large quantities of carbon dioxide from carbon-dioxide-containing natural gas mixtures, as a preparatory step for the subsequent purification of the enriched-methane product by conventional absorption techniques.

3 Claims, 4 Drawing Figures

METHOD OF TREATING CARBON-DIOXIDE-CONTAINING NATURAL GAS

BACKGROUND OF THE INVENTION

As the value of petroleum crude continues to escalate, it will become increasingly more economical to employ enhanced oil-recovery techniques, specially for recovering heavy crude oils. One particularly advantageous enhanced recovery method is the injection of high pressure, substantially pure gaseous carbon dioxide into an oil well. This procedure takes advantage of carbon dioxide's high solubility in crude oil, together with the fact that the viscosity of the crude oil-carbon dioxide solution is significantly lower than the crude oil alone. Consequently, even heavy crude oils can be recovered by injecting the gaseous carbon dioxide into the subterraneous formation in an amount sufficient to saturate the contained oil, followed by the withdrawal of the low viscosity crude oil-carbon dioxide solution from the formation.

A direct consequence of this particular enhanced recovery technique, however, is that the gaseous phase recovered at the well head is contaminated with carbon dioxide, containing as much as 30–90 mol percent carbon dioxide. Since this carbon dioxide disadvantageously reduces the heating value of the recovered natural gas mixture, it must be removed prior to further use of the natural gas. At present, a variety of separation techniques are available for this purpose.

The most prevalent method currently practiced for removing carbon dioxide from gas streams is by a physical or chemical washing or absorption. Solvents commonly used for these procedures include: methanol, amines (e.g., monethanolamine and diethanolamine), propylene carbonate, potassium carbonate and N-methyl-pyrolidone. Unfortunately, with the absorption approach, both equipment size the operating expenses tend to be strongly influenced by the concentration of carbon dioxide in the gas stream to be treated. As the carbon dioxide concentration in the gas stream increase, the costs associated with the use and replacement of the absorption fluid tend to increase significantly. Additional expenses are also incurred for reactivation of the carbon dioxide loaded solvent. Moreover, even though such adsorption systems are designed to minimize thermodynamic inefficiencies, such inefficiencies are generally unavoidable in the regeneration system regardless of whether it operates on pressure differences, temperature differences or some combination thereof.

Adsorption systems have also been used to remove carbon dioxide from gas streams. However, besides being saddled with substantial irreversible energy losses, such systems are also generally limited to the removal of small quantitites of carbon dioxide from gas streams because of economic considerations.

Still another treatment approach employs cryogenic processing techniques. At low carbon dioxide concentrations, advantage is taken of the relatively high freezing point of carbon dioxide relative to the freezing point of other gases with which it is normally found in admixture, by allowing carbon dioxide to selectively freeze out or plate unto heat transfer surfaces; with the subsequent removal therefrom by flowing an essentially carbon dioxide-free gas stream thereover on a subsequent cycle. One skilled in this technology will recognize this as a standard procedure in the air separation arts. However, at higher carbon dioxide concentrations, cryogenic processing techniques have generally been thought to be inapplicable because of the likelihood that the freezing carbon dioxide will plug process piping and equipment, rendering the entire system inoperable. Notwithstanding this potential plugging problem, the potential for a more energy-efficient separation gives the cryogenic technique an inherent advantage relative to the other treatment options. For this reason, the prior art has attempted to define effective cryogenic techniques for rejecting large quantities of carbon dioxide from gas streams.

As early cryogenic approach is illustrated in U.S. Pat. No. 2,632,316—Eastman, which relies solely upon the partial condensation of the carbon-dioxide-containing natural gas for selectively removing carbon dioxide from the gas. As disclosed, the gas mixture is cooled against separated products, including work-expanded carbon dioxide product, at an elevated pressure to partially condense the gas mixture. The bulk of the carbon dioxide is then recovered with the condensed liquid phase; while the gas phase is recovered as the treated fuel gas product. As one skilled in this technology readily recognizes, the quantity and purity of the carbon dioxide removed and the purity of the methane product (treated fuel gas) produced by the Eastman process are determined solely by the temperatures and prevailing pressures during the single condensation and gas-liquid separation steps and will be severely limited by equilibrium mass transfer conditions.

U.S. Pat. No. 3,130,026—Becker, which integrates a step of rectification with the preliminary step of partial condensation, provides an improvement relative to the Eastman process. In the Becker process, as in the Eastman process, the feed gas is cooled against warming product streams including work-expanded carbon dioxide product, at an elevated pressure to partially condense the gas mixture. The non-condensed vapor fraction is then treated in a chemical or physical absorption system to remove its residual carbon dioxide content producing a methane enriched gas; while the condense liquid phase, containing the bulk of the carbon dioxide of the feed gas mixture, is treated to further increase its carbon dioxide concentration. This condensed liquid is initially reduced in pressure, to about 200 psia, for example, and is fed into the top of a rectification zone (stripping column). The liquid is separated into a methane-containing overhead vapor and a carbon-dioxide liquid. The overhead vapor is recycled for further processing with the feed gas mixture, while the liquid is recovered as the carbon dioxide product and is work-expanded to provide process refrigeration. The methane product is recovered from the absorption system at elevated pressure, for example, at about 45 atmospheres absolute; while the carbon dioxide is recovered at substantially atmospheric pressure.

While the Becker process does provide an improvement in the bulk separation of carbon dioxide from the carbon-dioxide-containing natural gas mixture relative to the prior-art Eastman process, it is not without its disadvantages. In the first place, although rectifying the carbon-dioxide-containing liquid stream recovered from the initial separation stage at a low superatmospheric pressure allows the production of a purer carbon-dioxide-containing liquid product, the concentration of carbon dioxide in the overhead vapor of this rectification stage is higher than would be the case at a higher rectification pressure. As a consequence, this overhead vapor cannot economically be treated directly in an absorption system to recover its methane content; instead Becker provides that this stream be recycled to the feed gas mixture. This partially enriched methane-containing vapor must now be reseparated from the feed gas. The energy needed to offset the irreversible energy losses occasioned by this processing method is reflected in the power demands of the recirculating compressor. If possible, such irreversibilities should be avoided. Moreover, rectification at the low superatmospheric pressure also economically inhibits the direct reuse of the separated carbon dioxide product in any enhanced oil recovery operation because of the need for significant recompression of the total carbon dioxide product.

Finally, in terms of the crude methane product produced, the Becker process is no better than the Eastman process since it also relies solely on partial condensation for generating the methane-enriched gas. Accordingly, the purity of the methane product is determined solely by the temperatures and prevailing pressures during the condensation and gas-liquid separation steps, and will be severely limited by equilbrium mass transfer conditions.

Besides the above-mentioned cryogenic processes for the bulk removal of carbon dioxide from gas streams, the prior art also includes cryogenic systems for producing pure products from the gas feed mixture. U.S. Pat. Nos. 4,149,864—Eakman et al and 4,152,129—Drentham et al typical examples. Both patents illustrate single-column rectification systems employing conventional overhead condensers and kettle reboilers. Although useful for producing pure overhead and kettle products, these systems tend to be very energy-intensive as a result of their need to regenerate a sizable methane liquid reflux stream for adequately rectifying the feed gas mixture. As a result, when ultra-high purity products need not be produced, these processes are not generally economically justifiable.

OBJECTS OF THE INVENTION

It is an object of this invention to provide an economical process for separating carbon dioxide from a carbon-dioxide-containing natural gas mixture with a low energy expenditure.

It is another object of this invention to provide a method for the bulk separation of carbon dioxide from an elevated-pressure carbon-dioxide-containing natural gas mixture, particularly when the gas contains a high concentration of carbon dioxide, by liquefying the carbon dioxide by cooling without the formation of solid carbon dioxide.

It is also an object of this invention to provide a method for the bulk separation of carbon dioxide from an elevated-pressure carbon-dioxide-containing natural gas mixture in a manner which reduces the energy expenditure required for reinjection of the carbon dioxide in an enhanced oil-recovery system.

It is a further object of this invention to provide a method for the bulk separation of carbon dioxide from an elevated-pressure carbon-dioxide-containing natural gas mixture using only the refrigeration potential of the pressurized raw natural gas stream itself.

It is a final object of this invention to avoid or remove the prior art deficiencies mentioned above by providing an improved cryogenic separation process for rejecting large quantities of carbon dioxide from a carbon-dioxide-containing natural gas mixture.

SUMMARY OF THE INVENTION

A method for separating carbon dioxide from a carbon-dioxide-containing natural gas mixture having a high carbon dioxide content comprising:
(1) liquefying a major portion of the carbon dioxide in the natural gas mixture by cooling the gas mixture, at an elevated pressure above about 700 psia,
(2) thereafter separating the cooled natural gas mixture of step (1) into a condensed liquid carbon-dioxide-containing stream and non-condensed vapor,
(3) subcooling the liquid carbon-dioxide-containing stream
(4) rectifying the subcooled liquid carbon-dioxide-containing stream to provide methane-containing overhead vapor and a kettle liquid having an increased carbon dioxide content,
(5) vaporizing a minor portion of the carbon-dioxide-containing kettle liquid of step (4) by heating so as to provide reflux vapor for rectifying the subcooled liquid carbon-dioxide-containing steam of step (4),
(6) separating a carbon-dioxide-enriched liquid from the vapor of step (5),
(7) combining the methane-containing overhead vapor separation of step (4) with the non-condensed vapor separated in step (2) to provide a methane-containing gas mixture,
(8) cooling the methane-containing gas mixture of step (7) and rectifying the cooled mixture to provide a methane-enriched overhead vapor and a kettle liquid containing carbon dioxide, the steps (1) through (8) being conducted at a pressure below the critical pressure and at a temperature above the triple point temperature for each composition involved.

Preferably, the various cooling and heating steps are conducted by indirect heat exchange between various internal streams; generally counter-current heat transfer is preferred.

Refrigeration necessary to sustain the cryogenic processing is preferably supplied by work expanding the methane-enriched overhead vapor separated in step (8).

According to this invention, the term "natural gas mixture" is used to mean a methane-containing gas which will generally be recovered from a subterranean formation, and will generally contain methane at a concentration from about 10% to 70%.

The phrase "heavy concentration of carbon dioxide" means a gas mixture having 30–90 mol percent carbon dioxide.

The term "heavy hydrocarbon" is intended to describe the class of paraffinic hydrocarbon compounds having two or more carbon atoms in their chemical structure.

The term "column is used to mean a rectification column, i.e., a contacting column, wherein liquid and vapor phases are countercurrently contacted to effect separation of a flu:d mixture as, for example, by contacting vapor and liquid phases in a series of vertically spaced-apart trays or plates mounted within the column or alternatively on packing elements with which the column is filled. For an expanded discussion, see the *Chemical Engineers Handbook*, 5th Edition, edited by R. H. Parry and C. H. Chilton, McGraw-Hill Book Co., New York, Section 13, "Distillation," B. D. Smith et al., page 13—3, *The Continuous Distillation Process*.

The term "stripping column" is used to describe that part of a distillation column which is below the feed stage as, for example, described in *Design of Equilbrium*

*Stage Processes,* B. D. Smith, McGraw-Hill Book Co., New York 1963, pp. 143–146.

DESCRIPTION OF THE INVENTION

The present invention comprises an improved cryogenic separation process for rejecting large quantities of carbon dioxide from a carbon-dioxide-containing natural gas mixture. The invention is particularly useful for treating the gas fraction recovered from a petroleum well practicing carbon dioxide injection as an enhanced recovery technique. The invention may also find application in treating naturally occurring gas wells having high quantities of carbon dioxide. In particular, the invention can be used to reject carbon dioxide from a natural gas mixture containing from about 30–90 mol percent carbon dioxide. The invention is preferably used in combination with a physical or chemical absorption system, wherein the cryogenic techniques of this invention are initially used to remove large amounts of carbon dioxide from the natural gas mixture followed by solvent treatment to produce a high-purity natural gas product. In effect, this combination allows one to realize the advantages of both treatment approaches while avoiding many of their disadvantages.

Figure 1:
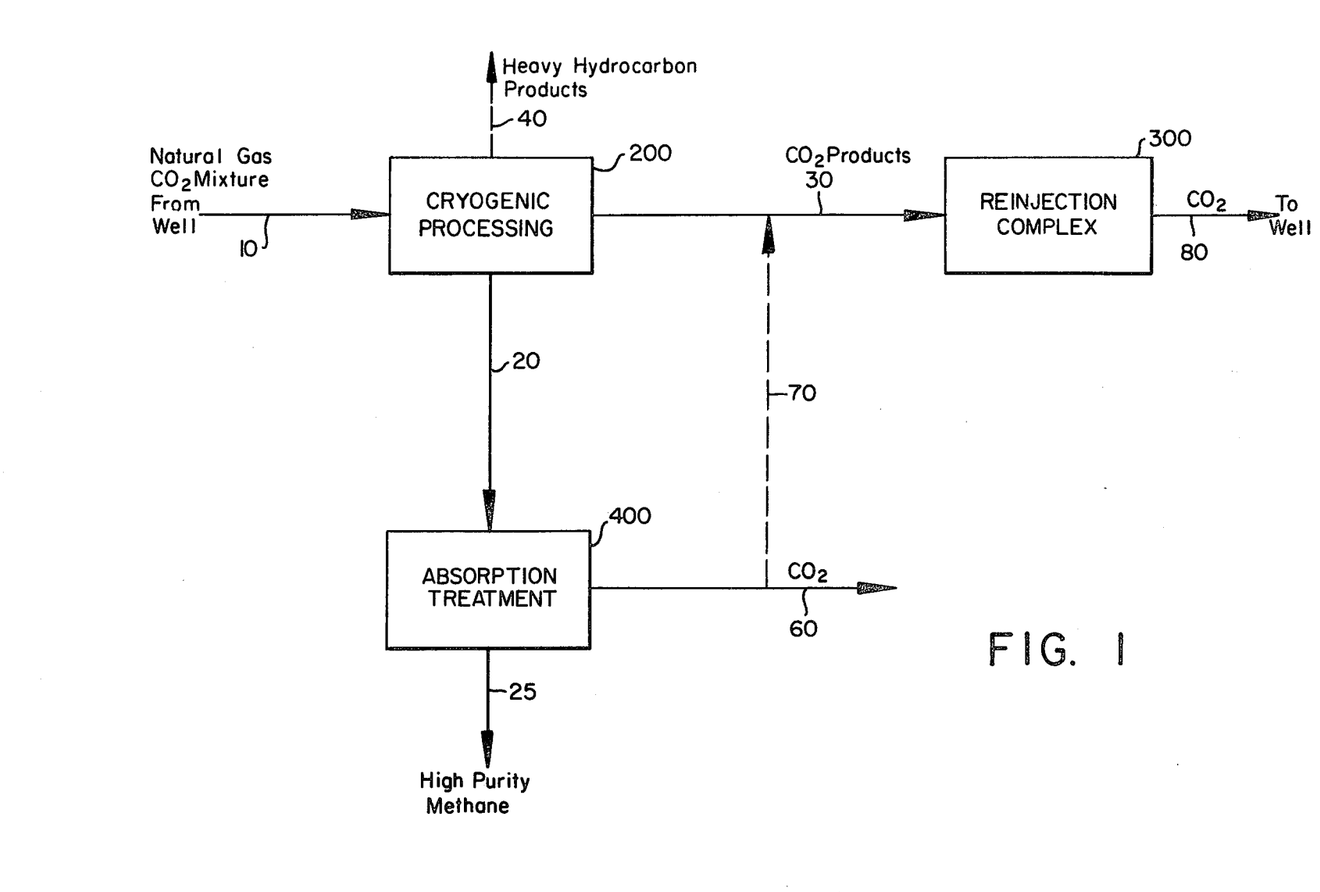
FIG. 1 is a block flow diagram illustrating the integration of this invention into an overall carbon dioxide injection system for producing pipeline quality natural gas.

The use of this invention in connection with a carbon dioxide injection system is illustrated in the block flow diagram of FIG. 1. The well-head gas fraction, recovered from a petroleum field practicing carbon dioxide injection, is admitted through conduit 10 into the cryogenic processing unit 200 of this invention. Detailed flow arrangements for the cryogenic processing unit are discussed hereafter in connection with FIGS. 2 and 3. The cryogenic processing unit 200 separates the natural gas mixture delivered through conduit 10 into a methane-enriched product in conduit 20 and various carbon dioxide products, represented schematically by line 30. Alternatively, the cryogenic processing unit may also produce a heavy hydrocarbon product, represented by dotted line 40.

The methane-enriched product of the cryogenic processing unit in line 20 is subsequently delivered to the absorption treatment system 400. In the absorption treatment system, the methane-enriched product is treated with one of the generally well-known carbon dioxide solvents; e.g., methanol, to generate a high purity natural gas product; e.g., suitable for introduction into natural gas pipelines. The spent carbon-dioxide-containing solvent is regenerated and recycled for absorption treatment of the methane-enriched gas; while the so-removed carbon dioxide is rejected from the absorption treatment system through line 60. If appropriate, this gas may be combined with one of the carbon dioxide products, represented schematically by line 30, by passage through line 70. The high purity methane product is recovered in line 25.

The carbon dioxide products, line 30, are delivered to a reinjection complex 300 where any necessary treatment steps, including recompression, are conducted for reuse of the carbon dioxide for oil well injection through line 80.

Figure 2:
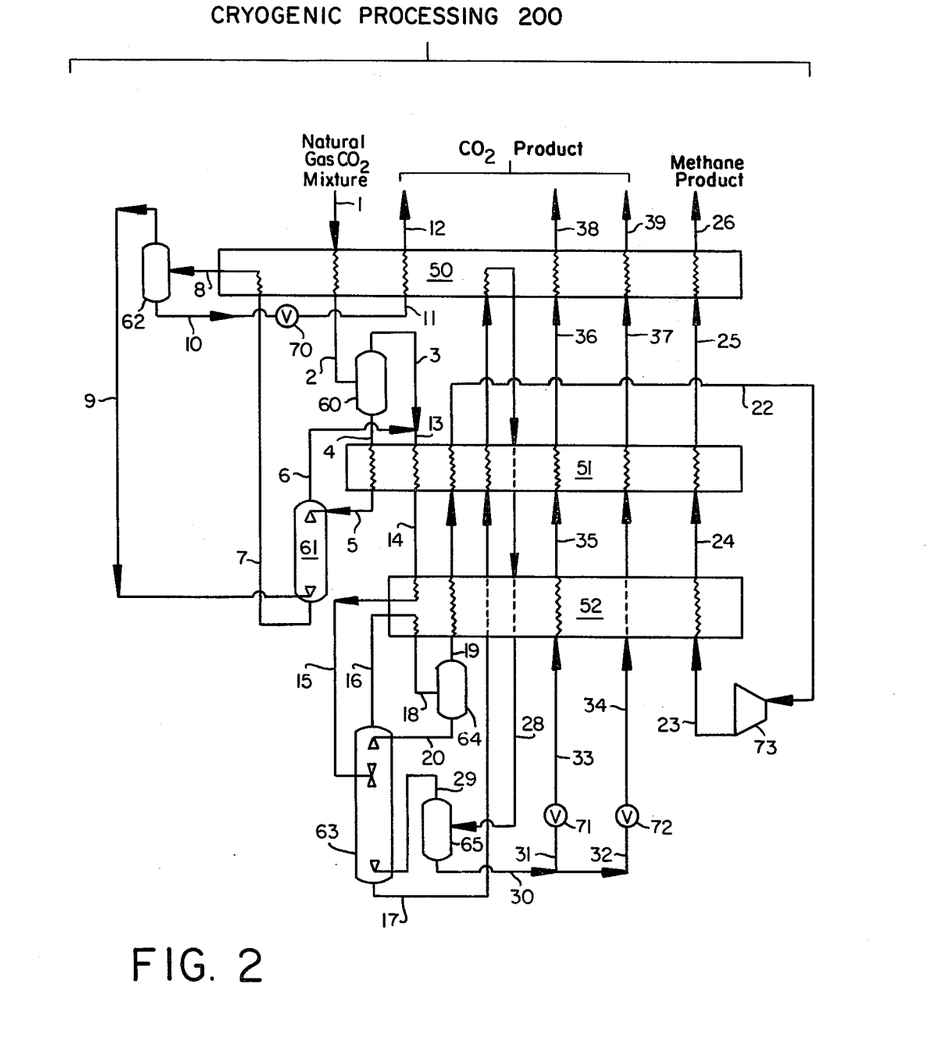
FIG. 2 is a schematic representation of one embodiment of the cryogenic process of this invention for the bulk removal of carbon dioxide from a carbon-dioxide-containing natural gas mixture.

Referring now to FIG. 2, there is illustrated in detail a cryogenic processing unit 40 suitable for treating a natural gas mixture recovered from a petroleum well practicing carbon dioxide injection. This system is designed to separate the feed gas mixture into carbon dioxide and methane-enriched products. In this embodiment, the carbon dioxide is recovered at three different pressure levels; for example, with the feed gas mixture supplied at about 700 psia; e.g., a typical natural gas well-head pressure, the carbon dioxide may be recovered at 550, 360 and 200 psia.

An elevated pressure, dry natural gas mixture is introduced for cooling into heat exchanger 50 through conduit 1. Since water will freeze and plug process piping under the operating conditions of the present invention, it must be removed prior to treatment in the apparatus of FIG. 1. Water may be removed by any of the procedures well-known to those skilled in this technology; for example, by molecular sieve adsorption.

In order to avoid carbon dioxide solidification in the process of FIG. 2, the natural gas mixture must be supplied at a pressure high enough so that during cooling in any of the heat exchange steps, to be more fully described hereinafter, none of the cooling gas streams reach the triple-point temperature for their respective composition. Generally, by introducing the natural gas mixture into heat expander 50 at a pressure above about 700 psia, carbon dioxide freezing conditions can be avoided. At the opposite extreme, the natural gas mixture must also be treated at a pressure below its critical pressure. As one skilled in this technology will readily recognize, complete separation of the constituents of the gas mixture is impossible above the critical pressure since the physical characteristics of the liquid and vapor phases become identical, both phases existing as a single intermixed fluid. Generally, by introducing the natural gas mixture into heat exchanger 50 at a pressure below about 1000 psia, problems created by exceeding critical limits will be avoided.

The natural gas mixture in conduit 1 is cooled; e.g., to about 270° K., in heat exchanger 50 against warming product streams so as to condense a major portion; e.g., 50 to 95 mol percent, of its carbon dioxide content. The partially liquefied gas in conduit 2 is then introduced into separator 60 wherein the carbon-dioxide-containing condensed liquid stream is separated and recovered in conduit 4 from the non-condensed vapor recovered in conduit 3. The liquid in conduit 4 is subcooled in heat exchanger 51; e.g., to about 260° K., also against warming product streams, and is in roduced into stripping column 61 through conduit 5. A stripping column is used beause the additional energy that would be needed to generate a reflux liquid flow sufficient to provide a high-purity methane overhead produce as, for example, disclosed in U.S. Pat. Nos. 4,149,864 and 4,152,129, would require more refrigeration than can generally be economically obtained from the natural gas mixture alone. In stripping column 61, the light components of the subcooled liquid, for example nitrogen and methane, are preferentially removed with the overhead vapor through condit 6. Reflux vapor for column 61 is preferably generated by vaporizing a minor portion; e.g., 10 to 45 mol percent, the kettle liquid of column 61 recovered in conduit 7 against the cooling natural gas mixture in heat exchanger 50. The partially vaporized stream is removed from heat exchanger 50 through conduit 8 and is introduced into separator 62. The vapor fraction recovered in conduit 9 is then introduced as reflux vapor into the kettle of stripping column 61. The liquid stream recovered in conduit 10 is throttled to a lower pressure through valve 70; for exmaple, if the natural gas mixture in conduit 1 is supplied at about 700 psia, then the liquid in conduit 10 may be throttled to about 550 psia through valve 70. In this particular embodiment, the throttled liquid in conduit 11 is heated against the cooling natural gas mixture in heat exchanger 50 and is recovered as a high-pressure carbon dioxide product in conduit 12.

According to this invention, stripping column 61 is preferably operated at a high supersatmospheric pressure, between about 500 and 1000 psia; e.g., 700 psia. In many cases, the stripping column will be conveniently operated at the same pressure as the natural gas mixture in conduit 1, neglecting unavoidable process-related pressure losses. Although conducting this separation at a high superatmospheric pressure tends to sacrifice the carbon dioxide purity of the kettle liquid by forcing more of the light components into this liquid, the carbon dioxide content of the overhead gas recovered in conduit 6 is low enough to avoid the need for recycling this gas to feed, and instead this gas can be directly treated for recovery of a methane-enriched product. Nevertheless, by a single step of fractional reboil, the kettle liquid can, if desired, be made more suitable for carbon dioxide reinjection purposes. More importantly, by conducting the separation in stripping column 61 at the higher pressure level, the recovered carbon dioxide products retain some of the pressurization of the original natural gas mixture, thereby reducing subsequent carbon dioxide recompression requirements. Additionally, problems with carbon dioxide solidification are also more safely avoided at the higher pressures.

Returning now to the non-condensed vapor recovered from separator 60 in conduit 3, this particular stream is mixed with the overhead vapor 6 of stripping column 61 and the resultant methane-containing gas mixture is introduced into heat exchanger 51 for cooling through conduit 13. The cooled methane-containing gas mixture is removed from heat exchanger 52 for further cooling; e.g., to about 245° K. The methane-containing gas mixture is cooled against warming product streams, whereby a significant portion of its residual carbon dioxide content condenses, and is then introduced into rectification column 63 through conduit 15 preferably as a two-phase mixture of methane-containing vapor and methane-containing liquid. A single-phase process stream can be utilized although an energy penalty will be incurred.

In rectification column 63, both phases of the methane-containing mixture are rectified to provide a methane-enriched overhead vapor product, recovered from separator 64 through conduit 19, and an additional carbon dioxide kettle liquid product stream, recovered from separator 65 through conduit 30. The operating pressure for column 63 is preferably the same as for column 61. The overhead vapor stream in conduit 16 is partially condensed in heat exchanger 52 to generate reflux liquid for column 63 and is then introduced into separator 64 through conduit 18. The reflux liquid thus produced is delivered to column 63 through conduit 20 while, as mentioned above, the methane-enriched vapor product, is recovered in conduit 19. Reflux vapor for column 63 is generated by partially vaporizing the kettle liquid, removed in conduit 17 by sequential heating in heat exchangers 51 and 50. The partially vaporized stream is then introduced through conduit 28 into separator 65 wherein reflux vapor for column 63 in conduit 29 is separated from the above-mentioned carbon dioxide product recovered in conduit 30.

In preferred practice, the refrigeration requirements of the process are supplied solely by the refrigeration potential of the pressurized natural gas mixture itself. In this embodiment, refrigeration is developed through a combination of the Joule-Thompson expansion of the carbon dioxide product streams and the work expansion of the methane-enriched product; the bulk of the refrigeration is supplied by the work expanded methane-enriched product. The refrigeration potential of the methane-enriched product in conduit 19 is first recovered by heat exchange with cooling gas and liquid streams in heat exchangers 52 and 51. The superheated vapor recovered from heat exchanger 51 in conduit 22 is then work expanded (e.g., from 700 psia to 1500 psia) through expansion device 73. Expansion device 73 may be an expansion turbine of conventional design. The work produced by this expansion process may, for example, be used for either gas compression or for generating electricity. The expanded and thereby cooled (e.g., to about 205° K.) methane-enriched product in conduit 23 is then conducted serially through heat exchangers 52, 51 and 50 and conduits 24 and 25 to satisfy the refrigeration duties of the cooling gas and liquid streams. The methane-enriched product is then recovered in conduit 26. The carbon dioxide liquid stream recovered from separator 65 in conduit 30 is divided into two streams in conduits 31 and 32 and each stream is throttled to a lower superatmospheric pressure through valves 71 and 72, respectively. In the embodiment illustrated in FIG. 2, stream 31 is throttled to a lower superatmospheric pressure than stream 32. For example, if the natural gas mixture in conduit 1 is supplied at a pressure of about 700 psia, a minor fraction of the liquid in conduit 30 is conducted through conduit 31 and may be throttled to about 200 psia (yielding a temperature of about 235° K.) while the other major fraction of the liquid in conduit 30 is conducted through conduit 32 and may be throttled to about 360 psia (yielding a temperature of about 250° K.). The throttled carbon dioxide liquid recovered in conduit 33 is conducted serially through heat exchangers 52, 51 and 50 in conduits 35 and 36 and is recovered as the low-pressure carbon dioxide product in conduit 38. In a similar fashion the throttled carbon dioxide liquid in conduit 34 is conducted through heat exchanger 51, conduit 37 and heat exchanger 50 and is recovered as a medium-pressure carbon dioxide product in conduit 39.

Figure 3:
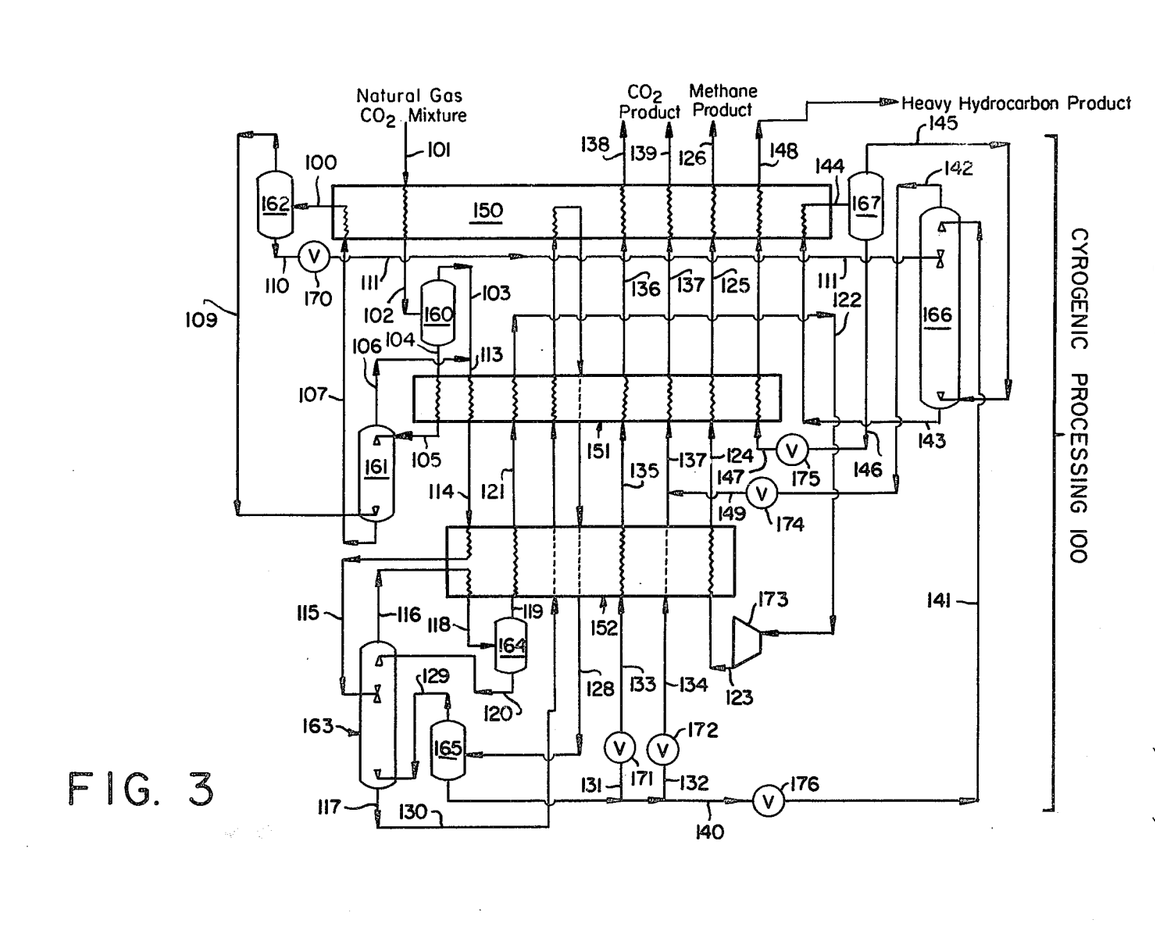
FIG. 3 is a schematic representation of another embodiment of the cryogenic process of this invention in which a heavy hydrocarbon product stream is also produced.

Referring next to FIG. 3, a further embodiment of a cryogenic processing unit 40' is illustrated in which a heavy hydrocarbon fraction is separately recovered as an additional product. In this embodiment, those processing steps equivalent to the gas treatment sequence of FIG. 2 are given the same reference numberal increased by 100. According to this embodiment, the natural gas mixture in conduit 101 is treated in the same manner as in FIG. 2, to generate medium- and low-pressure carbon dioxide products in conduits 139 and 138, respectively, and a methane-enriched product in conduit 126. However, in this embodiment, the carbon dioxide liquid recovered in conduit 110 from separator 162 is not removed as a high-pressure carbon dioxide product but rather is further treated to recover its heavy hydrocarbon content.

The carbon dioxide liquid in conduit 110 is throttled to a lower pressure through valve 170 and is introduced into rectification column 166 through conduit 111. This feed is rectified to produce a carbon dioxide overhead gas in conduit 142 and a heavy hydrocarbon enriched kettle liquid in conduit 143. A portion of the liquid carbon dioxide recovered from separator 165 is used to reflux column 166 by passing this liquid through conduit 140, valve 176 and conduit 141. Vapor reflux is provided by partially reboiling the kettle liquid product 143 in heat exchanger 150, separating the so-produced vapor in conduit 145 and introducing this vapor into the bottom of column 166. The overhead carbon dioxide gas recovered in conduit 142 is added to the medium-pressure carbon dioxide product stream subsequently recovered in conduit 139 by flowing this gas through valve 174 and conduit 149.

The heavy hydrocarbon product is produced from the enriched heavy hydrocarbon kettle liquid recovered from column 166 in conduit 143. As noted, this liquid is partially reboiled in heat exchanger 150 by heat exchange with the cooling natural gas mixture, and the liquid and vapor fractions so-produced are separated in separator 167. The vapor fraction is used as reflux for column 166, while the liquid fraction is recovered in conduit 146 as the heavy hydrocarbon product. This liquid is passed through valve 175 and conduit 147 for sequential heat exchange with the cooling gas streams in heat exchangers 151 and 150. The heavy hydrocarbon product is then recovered in conduit 148.

Tables A and B present approximate mass balance results for computer modeling of the FIGS. 2 and 3 embodiments, respectively. In both approcahes, over 90% of the carbon dioxide contained in the natural gas mixture is recovered for reuse as a well-injection fluid, while about 70% of the methane is concentrated in the methane-enriched product for further treatment and recovery in an integrated absorption system. The FIG. 3 embodiment concentrates about 30% of the heavy hydrocarbons into one stream. This stream would typically contain essentially all of the butane and pentane fractions of the natural gas mixture, as well as a large portion of its propane content. The data contained in Tables A and B clearly illustrate the primary purpose of the cryogenic treatment system of this invention; i.e., the removal and recovery of a substantial portion of the carbon dioxide content of a natural gas mixture containing a high concentration of carbon dioxide. As illustrated, the natural gas mixture is supplied at a pressure of 700 psia and a flow rate of 1000 lb-mole/hr and contains 77% carbon dioxide and about 11% methane. If one were to treat this stream for carbon dioxide removal by purely absorption techniques, the solvent use rate would be on the order of 770×lb-moles/hr; where 770 is the quantity of carbon dioxide to be removed and X is the quantity of solvent needed to remove each lb-mole of carbon dioxide from the natural gas mixture. By employing the present invention, however, which only needs a portion of the energy content of the natural gas mixture itself, one is able to produce a concentrated methane stream containing about 70% of the methane with a carbon dioxide contaminant level of only about 30%. More precisely, by using the present invention, one is able to produce a methane-enriched product stream having a flow rate of about 149 lb-moles/hr with a carbon dioxide content of only 33%. Now, to remove the carbon dioxide from this stream in an absorption process, the solvent use rate need only be on the order of 49×lb-moles/hr, a reduction of about 94% from the absorption-only system. As one should readily appreciate from this simplified example, the present invention offers significant economic advantage as a bulk carbon dioxide separation process when used in combination with an absorption system.

Figure 4:
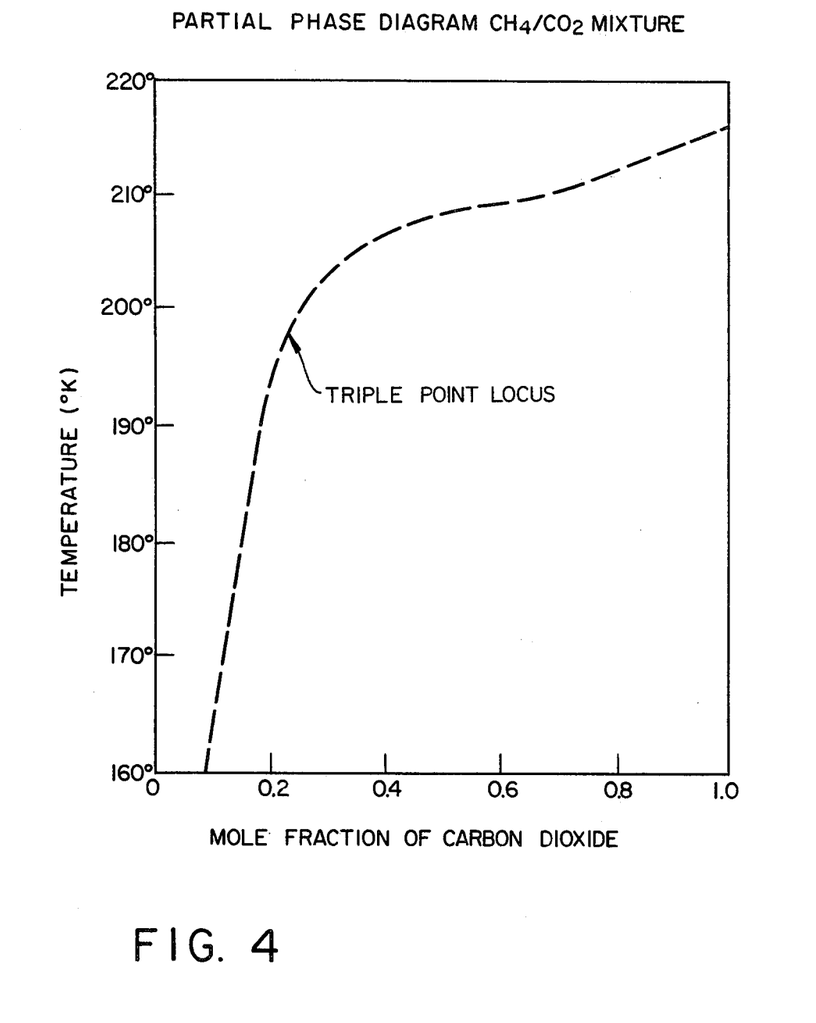
FIG. 4 is a graph, obtained from U.S. Pat. Nos. 2,888,807 and 4,152,129, showing the triple-point temperature locus for a carbon dioxide-methane binary system.

As indicated in the summary recitation of our invention, the invention process must be operated under temperature and pressure conditions that avoid the formation of solid carbon dioxide. In particular, the process steps must be conducted at a temperature above the triple-point temperature for the composition of each respective fluid at any step in the process. In effect, for the gas phases present, the carbon dioxide must remain above its triple point at its partial pressure. The locus of the triple-point temperature for the carbon dioxide-methane binary system is shown in FIG. 4. One skilled in this art will recognize that the presence of other components will change the position of the triple-point locus.

TABLE A

CARBON DIOXIDE & METHANE-ENRICHED PRODUCTS

| | | Carbon Dioxide Products | | | Methane- |
| --- | --- | --- | --- | --- | --- |
| | Feed | High Press. | Med. Press. | Low Press. | Enriched Product |
| Stream No. | 1 | 12 | 39 | 38 | 26 |
| Pressure (psia) | 700 | 550 | 360 | 200 | 150 |
| Flow Rate (lb/mol/hr) | 1000 | 558 | 171 | 122 | 149 |
| Gas Composition (%) | | | | | |
| Nitrogen | 2.1 | 0.3 | 0.2 | 0.2 | 12.5 |
| Methane | 10.7 | 3.8 | 4.4 | 4.4 | 49.3 |
| Carbon Dioxide | 77.3 | 84.0 | 86.8 | 86.8 | 33.1 |
| Heavy Hydrocarbon | 9.9 | 11.9 | 8.6 | 8.6 | 5.1 |

TABLE B

CARBON DIOXIDE, METHANE ENRICHED & HEAVY HYDROCARBON PRODUCTS

| | | Carbon Dioxide Products | | Methane- | Heavy Hydro- |
| --- | --- | --- | --- | --- | --- |
| | Feed | Med. Press. | Low Press. | Enriched Product | carbon Product |
| Stream No. | 101 | 139 | 138 | 126 | 148 |
| Pressure (psia) | 700 | 360 | 200 | 150 | 360 |
| Flow Rate (lb/mol/hr) | 1000 | 677 | 122 | 149 | 52 |
| Gas Composition (%) | | | | | |
| Nitrogen | 2.1 | 0.3 | 0.2 | 12.5 | |
| Methane | 10.7 | 4.2 | 4.4 | 49.3 | |
| Carbon Dioxide | 77.3 | 87.5 | 86.7 | 33.1 | 48.0 |
| Heavy Hydrocarbons | 9.9 | 8.0 | 8.7 | 5.1 | 52.0 |

What is claimed is:

1. A method for separating carbon dioxide from a carbon-dioxide-containing natural gas mixture having a high carbon dioxide content comprising:

(1) providing a natural gas mixture containing about 10 to 70% methane and having a carbon dioxide content of 30 to 90 mol percent and liquefying a major portion of the carbon dioxide in the natural dioxide in the natural gas mixture by cooling the gas mixture, at an elevated pressure above about 700 psig,
(2) thereafter separating the cooled natural gas mixture of step (1) into a condensed liquid carbon-dioxide-containing stream and non-condensed vapor,
(3) subcooling the liquid carbon-dioxide-containing stream,
(4) rectifying the subcooled liquid carbon-dioxide-containing stream to provide methane-containing overhead vapor and a kettle liquid having an increased carbon dioxide content,
(5) vaporizing a minor portion of the carbon-dioxide-containing kettle liquid of step (4) by heating so as to provide reflux vapor for rectifying the subcooled liquid carbon-dioxide-containing stream of step (4),
(6) separating a carbon-dioxide-enriched liquid from the vapor of step (5),
(7) combining the methane-containing overhead vapor separation of step (4) with the non-condensed vapor separated in step (2) to provide a methane-containing gas mixture,
(8) cooling the methane-containing gas mixture of step (7) and rectifying the cooled mixture to provide a methane-enriched overhead vapor and a kettle liquid containing carbon dioxide, the steps (1) through (8) being conducted at a pressure below the critical pressure and at a temperature above the triple point temperature for each composition involved.

2. A method in accordance with claim 1 wherein in step (8) the methane-containing gas mixture is cooled to provide a cooled mixture comprising methane-containing vapor and methane-containing liquid and both said liquid and said vapor are rectified to provide a methane-enriched overhead vapor and a kettle liquid containing carbon dioxide.

3. A method in accordance with claim 1 wherein the natural gas mixture of step (1) is at a pressure of about 700 to 1000 psig.

* * * * *